US007904316B2

(12) United States Patent
Brescia et al.

(10) Patent No.: US 7,904,316 B2

(45) Date of Patent: Mar. 8, 2011

(54) SYSTEM AND METHOD FOR GATHERING, MANAGING, AND ANALYZING PATIENT RECRUITMENT

(76) Inventors: Bonnie A. Brescia, Sherborn, MA (US); Joan F. Bachenheimer, Needham, MA (US)

( * ) Notice: Subject to any disclaimer, the term of this patent is extended or adjusted under 35 U.S.C. 154(b) by 470 days.

(21) Appl. No.: 12/016,725

(22) Filed: Jan. 18, 2008

(65) Prior Publication Data

US 2008/0177573 A1 Jul. 24, 2008

Related U.S. Application Data

(60) Provisional application No. 60/881,057, filed on Jan. 18, 2007.

(51) Int. Cl.
*A61B 5/00* (2006.01)
*G06F 19/00* (2006.01)

(52) U.S. Cl. .................................... 705/3; 705/2; 705/14

(58) Field of Classification Search .................. 705/2–3, 705/7, 10

See application file for complete search history.

(56) References Cited

U.S. PATENT DOCUMENTS

| | | | | |
|---|---|---|---|---|
| 2004/0093240 | A1 * | 5/2004 | Shah | 705/2 |
| 2007/0124767 | A1 * | 5/2007 | Laskowski-Bender et al. | 725/42 |
| 2007/0150296 | A1 * | 6/2007 | Ramcharran et al. | 705/1 |
| 2008/0133270 | A1 * | 6/2008 | Michelson et al. | 705/2 |

OTHER PUBLICATIONS

Bell, Direct-to-Consumer Prescription Drug Advertising, Apr. 2000, Journal of Family Practice.*

* cited by examiner

*Primary Examiner* — Luke Gilligan

(74) *Attorney, Agent, or Firm* — Peter A. Nieves; Sheehan Phinney Bass & Green PA

(57) ABSTRACT

A system and method for gathering, managing, and analyzing patient recruitment contains logic configured to receive patient marketing material from a source and logic configured to determine whether the patient marketing material is approved for use by a system administrator. The system also contains logic configured to provide the patient marketing material to a sponsor of a clinical study requiring patient recruitment, where the patient marketing material is provided to the sponsor for approval by the sponsor, and the system contains logic configured to determine if regulatory approval of the patient marketing material is required. Further, the system contains logic configured to make the patient marketing material available to a patient investigatory site for use in recruiting a patient for the clinical study.

12 Claims, 12 Drawing Sheets

Item Manager

| ITEM NAME | AUDIENCE | TYPE | REG ITEM | IS TOOL | RRK DECISION | CLIENT DECISION | MODIFIED | MODIFIED BY | VIEW | MODIFY | DELETE |
|---|---|---|---|---|---|---|---|---|---|---|---|
| Bookmark v1 | Patients | | Yes | Yes | Approved | Edits needed | 8/1/2006 | Greg Emmett | View | Modify | Delete |
| Bookmark v2 | Patients | | Yes | Yes | Approved | Edits needed | 2/27/2007 | Greg Emmett | View | Modify | Delete |
| Bookmark v3 | Patients | | Yes | Yes | Approved | Approved | 2/27/2007 | Greg Emmett | View | Modify | Delete |
| Call Center FAQ v1 | Health Care Consumer | | Yes | Yes | Approved | Approved | 10/25/2006 | Max Sponsor1 | View | Modify | Delete |
| Call Script v1 | Health Care Consumer | | Yes | Yes | Approved | Approved | 4/12/2007 | KK Rumril | View | Modify | Delete |
| Informed Consent Flipbook v1 | Enrollees | | Yes | Yes | Approved | Approved | 5/31/2007 | Erica Mercado | View | Modify | Delete |
| Magnet v1 | Health Care Consumer | | Yes | Yes | Approved | Pending | 4/23/2007 | Greg Emmett | View | Modify | Delete |
| News Letter v1 | Site Staff | | Yes | No | Approved | Approved | 6/13/2007 | Erica Mercado | View | Modify | Delete |

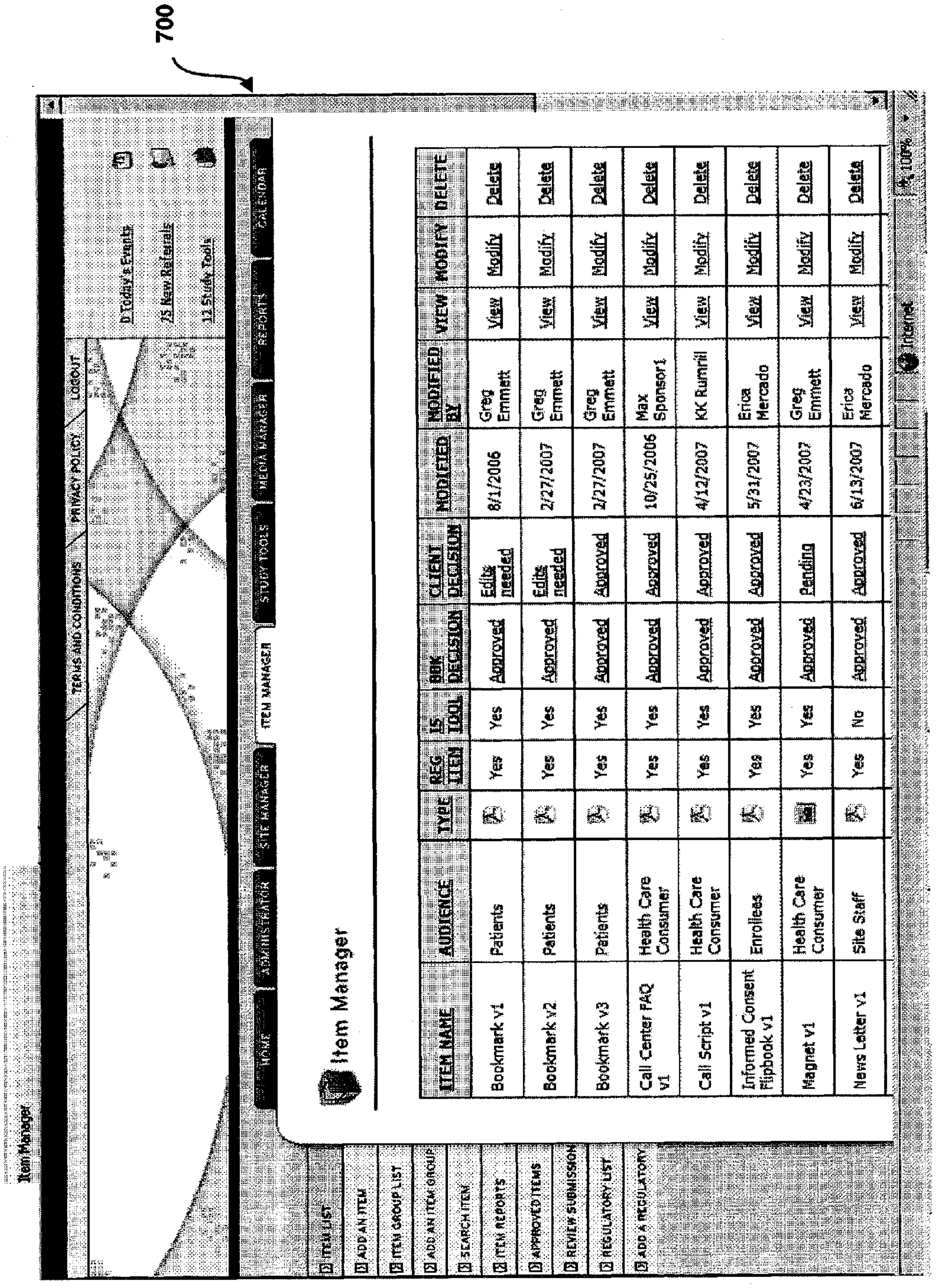

FIG. 10

Tool Manager

| TOOL NAME | TYPE | AUDIENCE | AVAILABILITY | MODIFIED BY | MODIFIED | VIEW |
|---|---|---|---|---|---|---|
| :30 TV spot v1 | | Health Care Consumer | Download | Greg Emmett | 2/27/2007 | View |
| Bookmark v1 | | Patients | Download | Greg Emmett | 2/27/2007 | View |
| Informed Consent Flipbook v1 | | Enrollees | Reorder | Erica Mercado | 5/31/2007 | View |
| Magnet v1 | | Enrollees | Initial Issue Only | KK Rumrill | 4/12/2007 | View |
| QAB Brochure v1 | | Enrollees | Download | Erica Mercado | 5/31/2007 | View |
| Patient Letter v1 | | Patients | Download | Erica Mercado | 5/31/2007 | View |
| Patient Web Site v1 | | Health Care Consumer | Initial Issue Only | KK Rumrill | 4/12/2007 | View |
| Poster v1 | | Patients | Reorder | KK Rumrill | 4/12/2007 | View |
| Print Advertisement v1 | | Health Care Consumer | Download | KK Rumrill | 4/12/2007 | View |

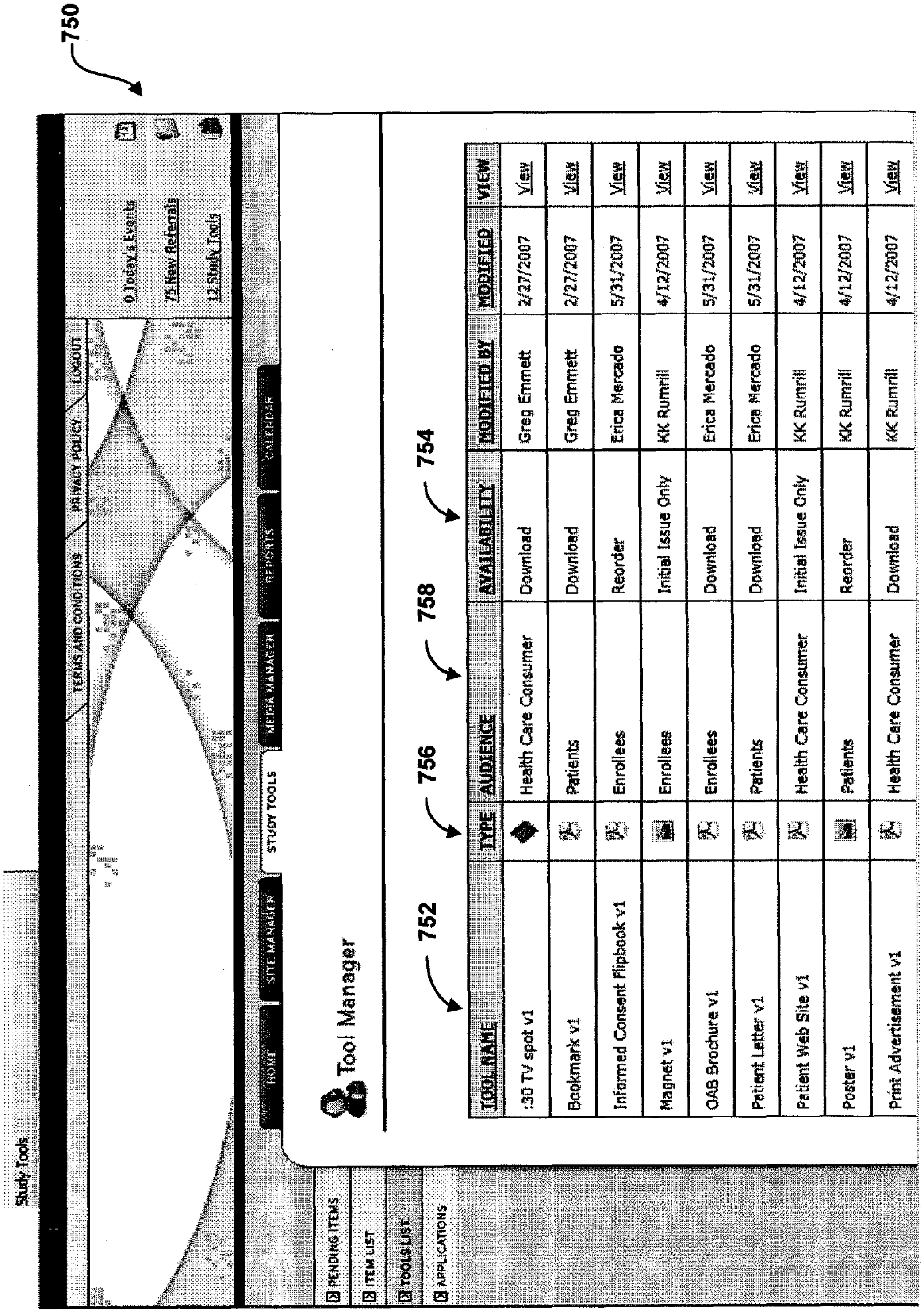

FIG. 11

SYSTEM AND METHOD FOR GATHERING, MANAGING, AND ANALYZING PATIENT RECRUITMENT

CROSS-REFERENCE TO RELATED APPLICATION

This application claims priority to copending U.S. Provisional Application entitled, "TrialCentralNet Service Suite," having Ser. No. 60/881,057, filed Jan. 18, 2007, which is entirely incorporated herein by reference.

FIELD OF THE INVENTION

The present invention is generally related to health care, and more particularly is related to a system and method for gathering, managing, and analyzing patient recruitment activities and related metrics.

BACKGROUND OF THE INVENTION

Within the fields of clinical research for pharmaceuticals, medical devices, and biologics, there are many electronic data collection and operational support systems known as clinical trial management systems or electronic data capture systems. Generally, in the patient recruitment process a company with a product, such as, but not limited to, a pharmaceutical company with a new drug, or a medical device company with a new medical device, have studies, also referred to as trials, that require completion to a degree of regulatory satisfaction. Such regulatory satisfaction may be as determined by organizations such as the Food and Drug Association (FDA). The company contracts with investigational sites for the completion of the studies, while the investigational sites are responsible for recruiting patients, having the studies completed, and reporting results of the studies.

Presently available systems address many aspects of interest to clinical research operations and management professionals, however, the solutions do not address the information-collection and process-management requirements of complex, multinational physician and patient recruitment, enrollment, and retention elements of their work.

Thus, a heretofore unaddressed need exists in the industry to address the aforementioned deficiencies and inadequacies.

SUMMARY OF THE INVENTION

Embodiments of the present invention provide a system and method for gathering, managing, and analyzing patient recruitment. Briefly described, in architecture, one embodiment of the system, among others, can be implemented as follows. The system contains logic configured to receive patient marketing material from a source and logic configured to determine whether the patient marketing material is approved for use by a system administrator. The system also contains logic configured to provide the patient marketing material to a sponsor of a clinical study requiring patient recruitment, where the patient marketing material is provided to the sponsor for approval by the sponsor, and the system contains logic configured to determine if regulatory approval of the patient marketing material is required. Further, the system contains logic configured to make the patient marketing material available to a patient investigatory site for use in recruiting a patient for the clinical study.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 10 is an example of an item manager screen provided by the recruitment system of FIG. 1.

FIG. 11 is an example of a tool manager screen provided by the recruitment system of FIG. 1.

DETAILED DESCRIPTION

As a central repository for data from multiple points such as, but not limited to, call centers, Clinical Trial Management Systems (CTMS), interactive voice response systems (IVRS), and study sites, the present system and method tracks individual patients from original inquiry through randomization, and provides a window into actual site performance metrics. The present system and method provides clinical trial sponsors with operational data and infrastructure needed to immediately and cost effectively establish situational awareness, and to anticipate recruitment needs and rapidly react to enrollment shortfalls. It should be noted that the present system is referred to herein as a recruitment system. In addition, the present system and method may be provided by a Web-based application for gathering, managing, and analyzing patient recruitment activities and related metrics. The following description assumes that the present system and method is provided by a Web-based application. It should be noted that the system and method may also be provided in an environment that is not Web-based.

The recruitment system of the invention can be implemented in software (e.g., firmware), hardware, or a combination thereof. In the currently contemplated best mode, the recruitment system is implemented in software, as an executable program, and is executed by a special or general purpose digital computer, such as a personal computer (PC; IBM-compatible, Apple-compatible, or otherwise), workstation, minicomputer, or mainframe computer. Specifically, the recruitment system, as provided by the computer, may be accessible via a Web site, through which parties using the recruitment system may interact. Further description of the recruitment system, and interaction therewith is provided below.

Figure 1:
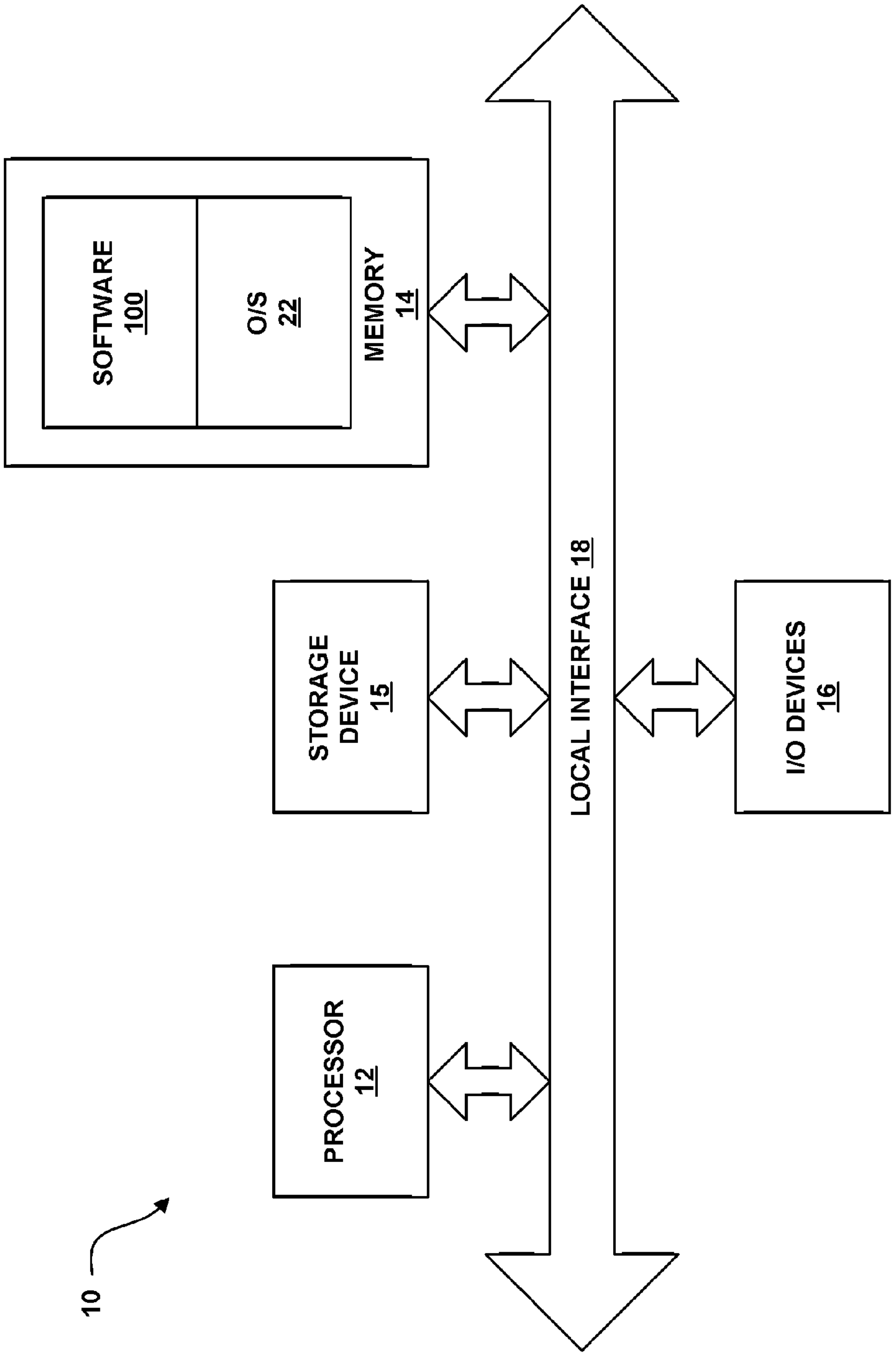
FIG. 1 is a schematic diagram illustrating an example of a general purpose computer that can implement the recruitment system of the present invention.

An example of a general purpose computer that can implement the recruitment system of the present invention is shown in FIG. 1. In FIG. 1, the recruitment system is denoted by reference numeral 10. It should be noted that communication with the recruitment system may be provided by multiple means such as, but not limited to, the Internet. Further description with regard to use of the recruitment system via use of the Internet is provided below.

Generally, in terms of hardware architecture, as shown in FIG. 1, the computer 10 includes a processor 12, memory 14, storage device 15, and one or more input and/or output (I/O) devices 16 (or peripherals) that are communicatively coupled via a local interface 18. The local interface 18 can be, for example but not limited to, one or more buses or other wired or wireless connections, as is known in the art. The local interface 18 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 12 is a hardware device for executing software, particularly that stored in the memory 14. The processor 12 can be any custom made or commercially available processor, a central processing unit (CPU), an auxiliary processor among several processors associated with the computer 10, a semiconductor based microprocessor (in the form of a microchip or chip set), a macroprocessor, or generally any device for executing software instructions.

The memory 14 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 14 may incorporate electronic, magnetic, optical, and/or other types of storage media. Note that the memory 14 can have a distributed architecture, where various components are situated remote from one another, but can be accessed by the processor 12.

The software 100 in memory 14 may include one or more separate programs, each of which comprises an ordered listing of executable instructions for implementing logical functions of the recruitment system, as described below. In the example of FIG. 1, the software 100 in the memory 14 defines the recruitment system functionality in accordance with the present invention. In addition, the memory 14 may contain an operating system (O/S) 22. The operating system 22 essentially controls the execution of computer programs and provides scheduling, input-output control, file and data management, memory management, and communication control and related services.

The recruitment system 10 may be provided by a source program, executable program (object code), script, or any other entity comprising a set of instructions to be performed. When a source program, then the program needs to be translated via a compiler, assembler, interpreter, or the like, which may or may not be included within the memory 14, so as to operate properly in connection with the O/S 22. Furthermore, the recruitment system 10 can be written as (a) an object oriented programming language, which has classes of data and methods, or (b) a procedure programming language, which has routines, subroutines, and/or functions.

The I/O devices 16 may include input devices, for example but not limited to, a keyboard, mouse, scanner, microphone, etc. Furthermore, the I/O devices 16 may also include output devices, for example but not limited to, a printer, display, etc. Finally, the I/O devices 16 may further include devices that communicate via both inputs and outputs, for instance but not limited to, a modulator/demodulator (modem; for accessing another device, system, or network), a radio frequency (RF) or other transceiver, a telephonic interface, a bridge, a router, etc.

When the recruitment system 10 is in operation, the processor 12 is configured to execute the software 100 stored within the memory 14, to communicate data to and from the memory 14, and to generally control operations of the computer 10 pursuant to the software 100. The recruitment system 10 and the O/S 22, in whole or in part, but typically the latter, are read by the processor 12, perhaps buffered within the processor 12, and then executed.

When the recruitment system 10 is implemented in software, as is shown in FIG. 1, it should be noted that the recruitment system 10 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The recruitment system 10 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the recruitment system 10 is implemented in hardware, the recruitment system 10 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 2:
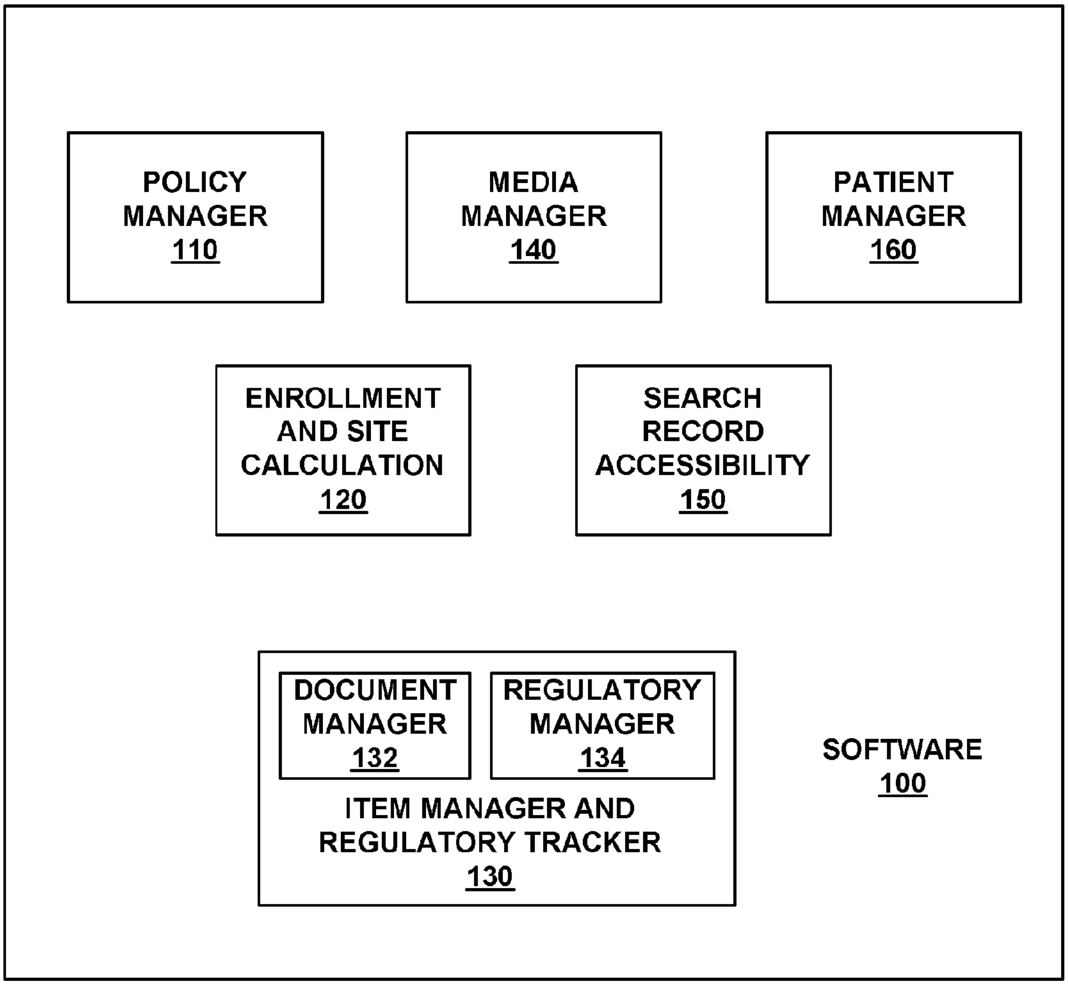
FIG. 2 is a schematic diagram further illustrating functional blocks representing functionality defined by the software of FIG. 1, in accordance with a first exemplary embodiment of the invention.

FIG. 2 is a schematic diagram further illustrating functional blocks representing functionality defined by the software 100 of FIG. 1, in accordance with a first exemplary embodiment of the invention. As is shown by FIG. 2, the software 100 defines a policy manager 110. The policy manager 110 defines levels of information access provided to users of the present recruitment system 10.

Examples of potential users of the recruitment system may include, but are not limited to, clinical study coordinators (study coordinators), sponsors, system administrators, monitors, investigators, clinical research coordinators, regulatory review boards, patient recruitment managers, and investigators. The following defines certain of the abovementioned.

Clinical research coordinator (CRC): The site administrator for a clinical study whose duties are usually delegated by a principal investigator. The CRC is a person at a medical or research facility that manages the daily activities of a clinical study, including coordination of the treatment or testing of patients. The CRC may also be referred to as a researcher, study coordinator, healthcare coordinator, data manager, research nurse, or protocol nurse.

Sponsor: an individual, company, institution, or organization taking responsibility for initiation, management, and financing of a clinical study. Usually the developer of the experimental drug, medical device, or treatment designs the study and pays for the trial.

Monitor: a person employed by a sponsor or a clinical research organization (CRO) to review study records to determine that a study is being conducted in accordance with the protocol. Duties of a monitor may include, but are not limited to, helping plan and initiate a clinical trial and assessing the conduct of trials. Monitors work with the clinical research coordinator to check all data and documentation from the clinical trial.

Investigator: A medical professional responsible for the overall conduct of a clinical trial at an investigational site. When more than one investigator is involved in a study, the group's leader is the principal investigator. Investigators include medical researchers in charge of carrying out a protocol of a clinical trial.

The policy manager 110 allows for an administrator of the recruitment system 10 to create a unique policy, which is a set of activities defined by the administrator. An activity is defined as an operation that is a command for adding, viewing, modifying, or deleting records. Policies allow the administrator to customize views and access rights to information provided by the present recruitment system 10. Examples of such information may include, but is not limited to, patient information and management reports. Specifically, due to regulatory restrictions, patient information should not be viewed by sponsors of a trial, while investigators conducting a trial should not have access to management reports that are reviewed by sponsors of the trial. Assigning policies to parties interacting with the recruitment system 10 allows for information control after a party logs into the recruitment system 10.

Each user of the recruitment system 10 is assigned a policy. Users are authenticated at a login process prior to being able to interact with the recruitment system 10, which directs the user to a customized view according to their assigned policy. This ensures a highly secure cyber environment for studying information and for communication. Personal views can be presented in any language with a simple modification of the policy. This dynamic functionality allows customization per user, per page, per function.

As is shown by FIG. 2, the software 100 also defines an enrollment and site calculation model 120. In accordance with the present invention, as defined by the enrollment and site calculation model 120, the recruitment system 10 may take investigatory site initiation data (SID), that is either inputted directly or received from a secondary source, and link the data to investigatory site randomization data and patient screening data. The patient screening data may be received from a secondary source such as, for example, an interactive voice response system (IVRS) or a clinical trial management system. The recruitment system 10 calculates the difference between SID and first patient randomized to create a new data point. The recruitment system 10 also allows for this data point to be aggregated and averaged by a number of variables including: site type (e.g., hospital-based, commercial research center, private practice), location (e.g., country, market, etc.), and physician specialty (e.g., oncology, urology).

The last patient screened date is compared to the date of the report (e.g., today's date as calculated by the system) to determine the difference between these dates to create an additional new data point. The recruitment system 10 allows for this data point to be aggregated and averaged by the same variables described above.

The recruitment system 10 then compares data points of each investigatory site to the mean, median, or mode, and identifies the amount and direction of variance, to provide direction on business interventions. The recruitment system 10 identifies trends in these data sets to track improvements or declines in individual investigatory site performance and study performance overall.

The specific combination of these data points into one analytic tool provided by the enrollment and site calculation model 120 provides a new layer of information not available in systems designed to support other processes in clinical trial management. Examples of sources of data from which data may be received by the present recruitment system 10 include, CTMS, electronic data capture software, patient diaries, IVRS, direct data entry, and general desktop software tools (e.g., Excel, Word, Access). These data sets have select data points which relate to various aspects of patient recruitment planning, implementation and redeployment, however, the present recruitment system 10 links the data points in a way that provides a platform specific to patient recruitment performance evaluation and decision-making. In addition, because the recruitment system 10 collects information from all of these sources on an ongoing basis, these reports are continuously refreshed with up-to-date information.

Examples of major categories of data sets include, investigators from investigatory sites, coordinators from investigatory sites, recruiters from investigatory sites, managers of sponsors, monitors of sponsors, managers of CROs, monitors of CROs, call centers of recruitment coordinators, media planners of recruitment coordinators, strategists of recruitment coordinators, regulatory bodies, protocols, study goals, recruitment tools, patient information, and status for each of the users, tools, patients, and sites. The present recruitment system 10 links information from these sets to each of the other sets.

As is shown by FIG. 2, the software 100 also defines an item manager and regulatory tracker 130. The item manager and regulatory tracker 130 is provided to track study documents through the earliest stages of development through final regulatory approvals. The item manager and regulator tracker 130 manages version control and regulatory approvals and can be tracked by individual item and by the user.

In accordance with the present invention, the item manager and regulator tracker 130 contains a document manager 132 and a regulatory manager 134. The document manager 132 is a central document repository for materials throughout the development cycle of the materials for use with the present recruitment system 10. The document manager 132 allows sponsors, sites, and regulatory bodies access to the most updated versions of materials and previously approved items. In accordance with the present invention, an item is a document or material that is available for use by the present recruitment system 10, however, the item has not yet obtained regulatory approval. Updates to items performed by the item manager and regulator tracker 130 may trigger an alert to a proper user of the recruitment system 10, that a change has been made to items available.

In accordance with the present invention, an item is posted by the recruitment system 10, on, for example, a Web site, and is assigned a specific level of approval formulated by an approval policy. Such an approval policy may be a policy implemented by A regulatory body. Based on the approval policy, each document, or item, is directed automatically through the appropriate approval channels. The approval policy ensures that each user only has access to the materials, or items, when the user needs to review or amend the materials or items, or is allowed to use the same.

The regulatory manager 134 provides functionality for regulating access of investigation sites to materials. Each regulatory body is linked to an investigatory site or sites. Once a site has been linked with a regulatory body, the site will only have access to materials that have been approved by that specific regulatory body. In the present description, prior to regulatory approval, materials that may potentially be used in a patient study, are considered items. However, after an item receives regulatory approval, the item is referred to herein as a tool, or a study tool. It should be noted that, in accordance with an alternative embodiment of the invention the investigatory site may have access to materials other than those that have been approved by the specific regulatory body.

The following is an example of using the document manager 132 and regulatory manager 134. For example, investigatory site A may be linked to a regulatory body RB1. The regulatory body RB1 reviews the materials or document and requires edits to the document. The edits are made and the document is reposted to the document manager 132 as a new version and resubmitted for review by the regulatory body RB1. Once the regulatory body RB1 approves the revised document, only site A will have access to that document. No other site will have access to that document.

The result after item approval, such as the document mentioned above, by the document manager 132 and regulatory manager 134, is a tool or study tool. Through study tools, access is provided to approved patient recruitment items, also referred to as tools. Visual representations and descriptions of each tool allows parties involved in patient recruitment to understand the purpose of an associated patient study enrollment campaign and its associated materials. In addition, study tools are linked with the item manager and regulatory tracker 130, ensuring that each user only views materials that have the correct approvals.

Figure 3A:
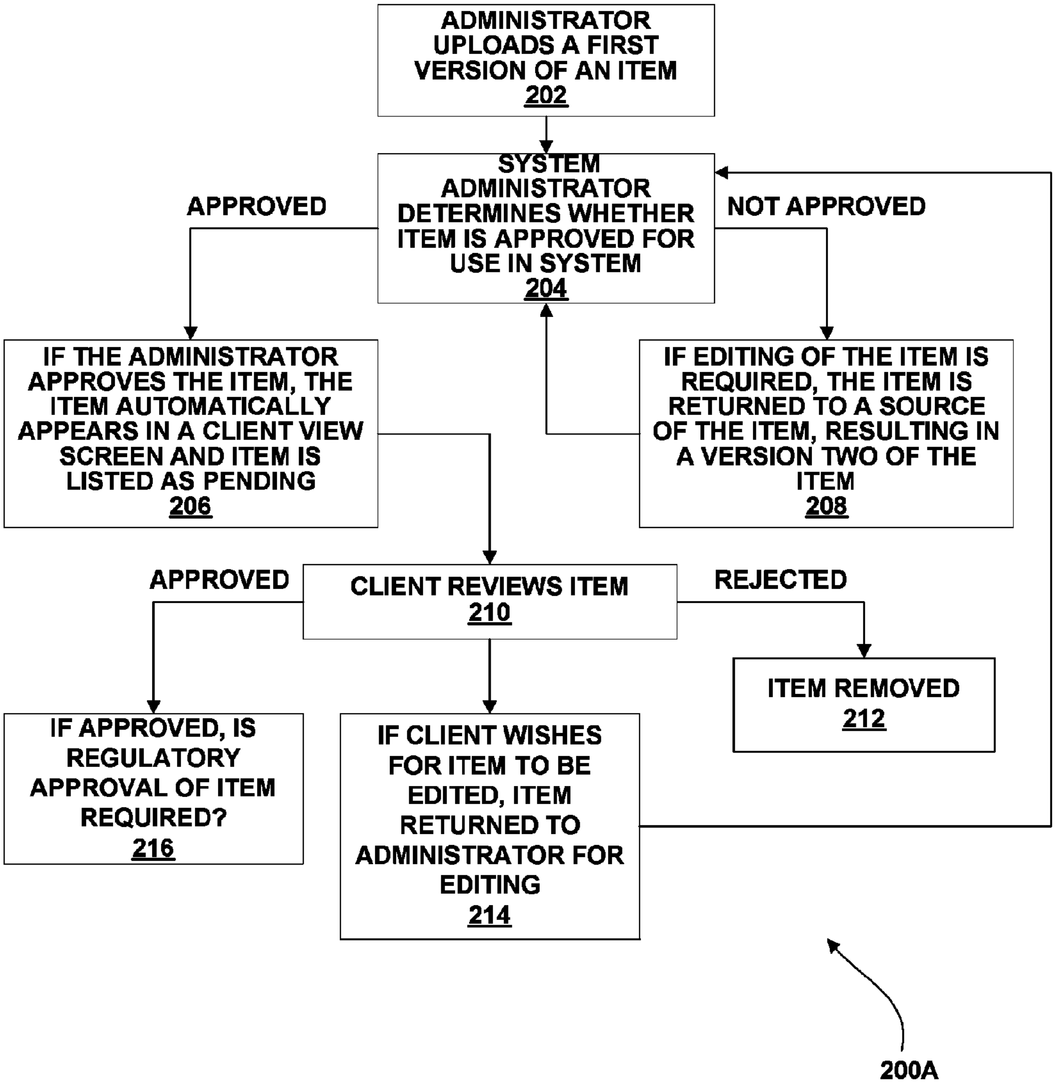
FIG. 3A and FIG. 3B are flowcharts further illustrating functionality performed by the item manager and regulator tracker of FIG. 2.
Figure 3B:
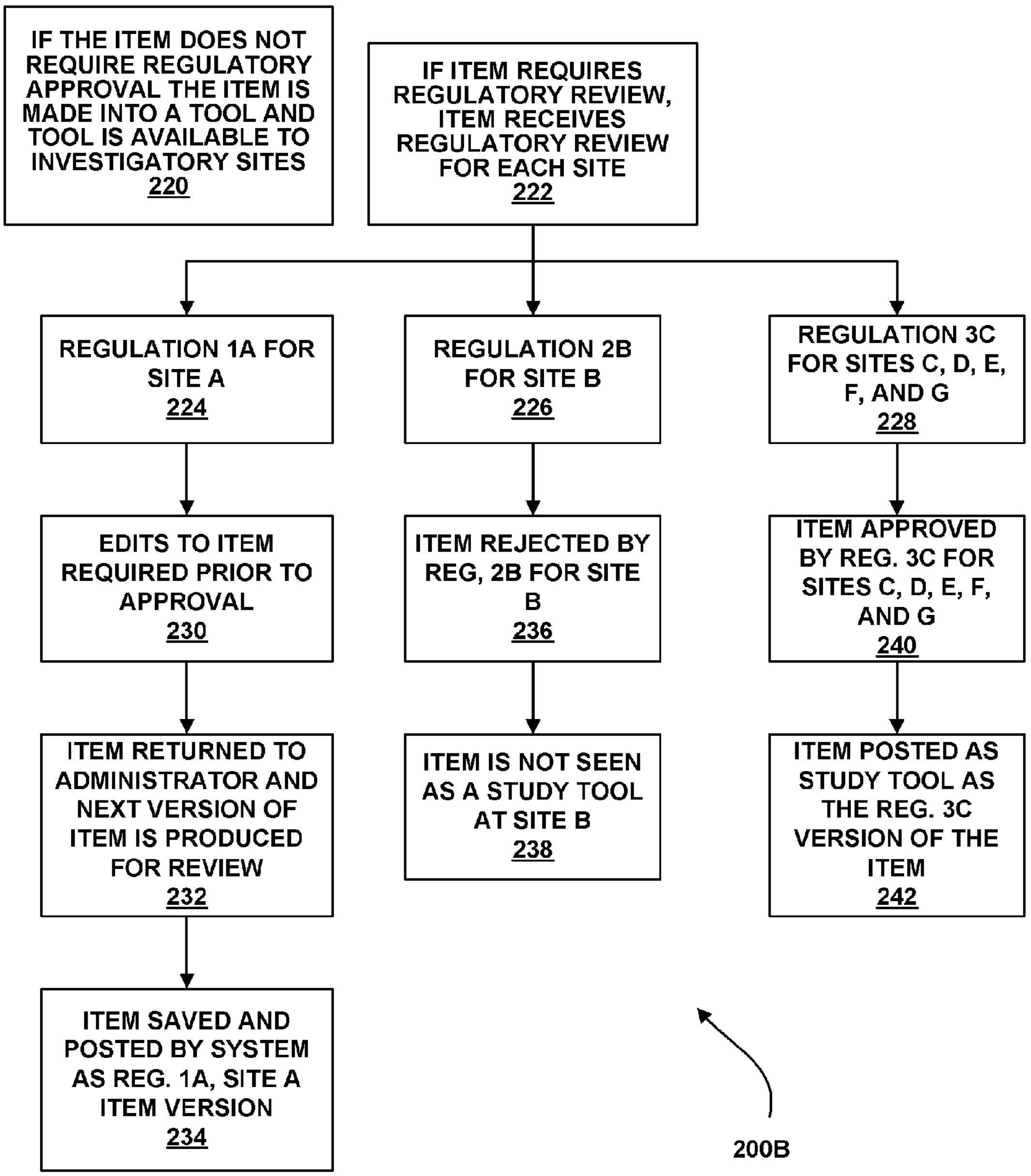
Figure 9:
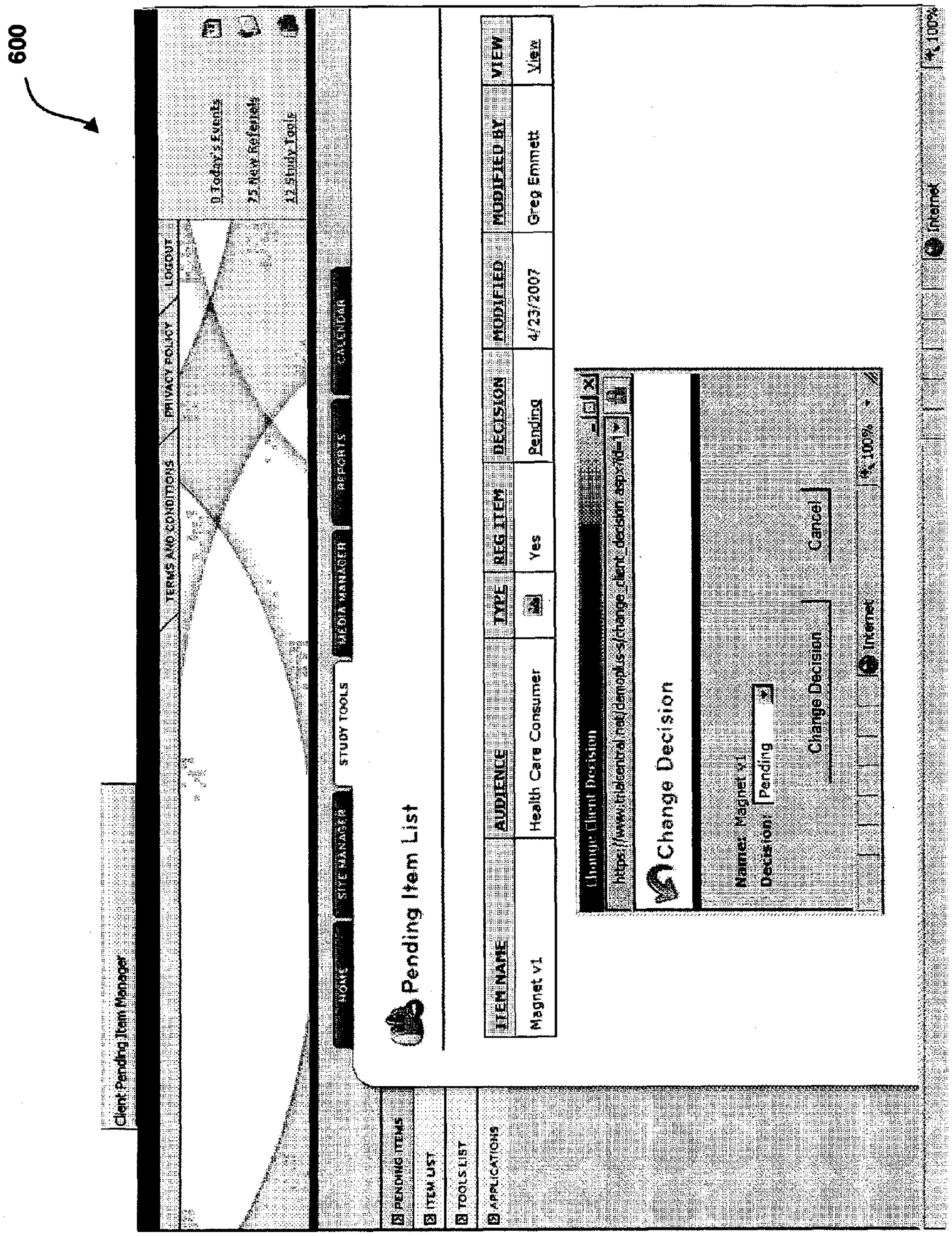
FIG. 9 is an example of a client view screen provided by the recruitment system of FIG. 1.

FIG. 3A and FIG. 3B are flowcharts 200A, 200B further illustrating functionality performed by the item manager and regulator tracker 130, specific to item approval and posting for seven investigatory sites. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved Referring to FIG. 3A, an administrator of the present recruitment system 100 may upload a first version of an item, which is a potential patient recruitment study tool (block 202). While there are many examples of items, one example may include a patient brochure. A patient recruitment system administrator then determines whether the item is approved for use in the patient recruitment system 10 (block 204). If the administrator approves the item, the item automatically appears in a client view for the client to review the item (block 206) and the item is listed as pending. An example of a client view screen 600 is shown by FIG. 9. It should be noted that the client is the sponsor. Alternatively, if editing of the item is required, the item is returned to a source of the item, resulting in a version two of the item (block 208) and the item is returned to the administrator for review.

As is shown by block 210, the client then reviews the item. If the client rejects the item, the item is removed from the client view and is no longer considered by the patient recruitment system 10 (block 212). If the client wishes for the item to be edited, the item is returned to the administrator for editing (block 214), where a next version of the item may be produced and the item review by the administrator starts again (block 204). Alternatively, as shown by block 216, if the client approves the item a determination is made as to whether regulatory approval of the item is required. As example of an item manager screen 700 is provided by FIG. 10.

As is legally required, regulatory approval is required prior to providing items to patients. Specifically, prior to an investigatory site being able to provide items to patients, regulatory approval is required. In the United States, one example of a regulatory body from which approval is required prior to allowing items to be provided to patients is the institutional review board. The institutional review board is an independent group of professionals designated to review and approve a clinical protocol, informed consent forms, clinical study advertisements and patient brochures, to ensure that the clinical study and associated trials are safe and effective for human participation. It is the institutional review board's responsibility to ensure that patients are protected and that the study adheres to United States Food and Drug Administration regulations. As is known by those having ordinary skill in the art, a protocol is a comprehensive plan describing the objectives, study design, methodology, statistical considerations and organization of a clinical trial. A study protocol must be approved by an Institutional Review Board or Independent Ethics Committee before investigational drugs can be administered to people.

In foreign countries, one example of a regulatory body from which approval is required prior to allowing items to be provided to patients, is an ethics committee. An ethics committee is an independent review board responsible for ensuring the protection of rights, safety, and well being of people participating in a clinical trial. Ethics committees are comprised of both medical and scientific professionals, and non-scientific people, and customarily review protocols and suitability of investigators and facilities, as well as methods and materials used to enroll patients.

FIG. 3B illustrates a flowchart 200B that is specific to addressing regulatory approval requirements and handling of the same. As is shown by block 220, if the item does not require regulatory approval, the item is made into a tool and the patient recruitment system 100 makes the tool available to investigatory sites, within a study tool section of the Web site provided by the patient recruitment software 10.

As shown by block 222, if the item is required to proceed through a regulatory review, the item receives a regulatory review for each investigatory site. In accordance with the present example, seven investigatory sites are considered where a site A is subjected to regulation 1A (block 224), site B is subjected to regulation 2B (block 226), and sites C, D, E, F, and G are subjected to regulation 3C (block 228).

FIG. 3B provides the example where regulation 1A requires edits to be performed to the item prior to approval (block 230). As shown by FIG. 3B, due to edits being required by regulation 1A, the item is returned to the administrator where a next version of the item may be produced and the item review by the administrator starts again (block 232). After approval of the next version of the item, the item is saved and posted by the patient recruitment system 100 as the regulation 1A, site A, item version (block 234). It should be noted that the item is not available until the next version is approved by the administrator, client, and regulation 1A.

FIG. 3B also provides the example where the item is rejected by regulation 2B for site B (block 236). In this example, the item will not be seen as a study tool at site B (block 238).

Referring to FIG. 3B, an example is also provided where the item is approved by regulation 3C for sites C, D, E, F, and G (block 240). In this situation, the item is approved without edits and the item is posted within the study tool section of the Web site provided by the patient recruitment software 10 as the regulation 3C version of the item (block 242).

An example of a tool manager screen 750 provided by the patient recruitment system 10 is provided by FIG. 11. As is shown by FIG. 11, the tool manager screen 750 contains a tool name column 752 providing names of approved study tools. In addition, the tool manager screen 750 shows the manner of availability of the study tool in an availability column 754. The type of file and category of audience are also provided within a type column 756 and an audience column 758, respectively.

Returning to FIG. 2, the software 100 also defines a media manager 140. Through functionality defined by the media manager 140, the patient recruitment system 10 provides financial management of advertising investment, tracks the effectiveness of the advertising, and ensures that the advertisement has the appropriate approvals in place by linking to the item manager and regulatory tracker 130.

The media manager 140 is used for financial management and tracking of return-on-investment (ROI). Specific to financial management, each investigatory site conducting a clinical trial can request financial support for advertising outreach to patients. Sponsors set the financial parameters for the project, and the patient recruitment system 10, via the media manager 140, ensures that each request falls within the approved budget. As well, the media manager 140 maintains a cumulative statement of what monies have been allocated, what has been invoiced, and what has been paid.

Figure 4:
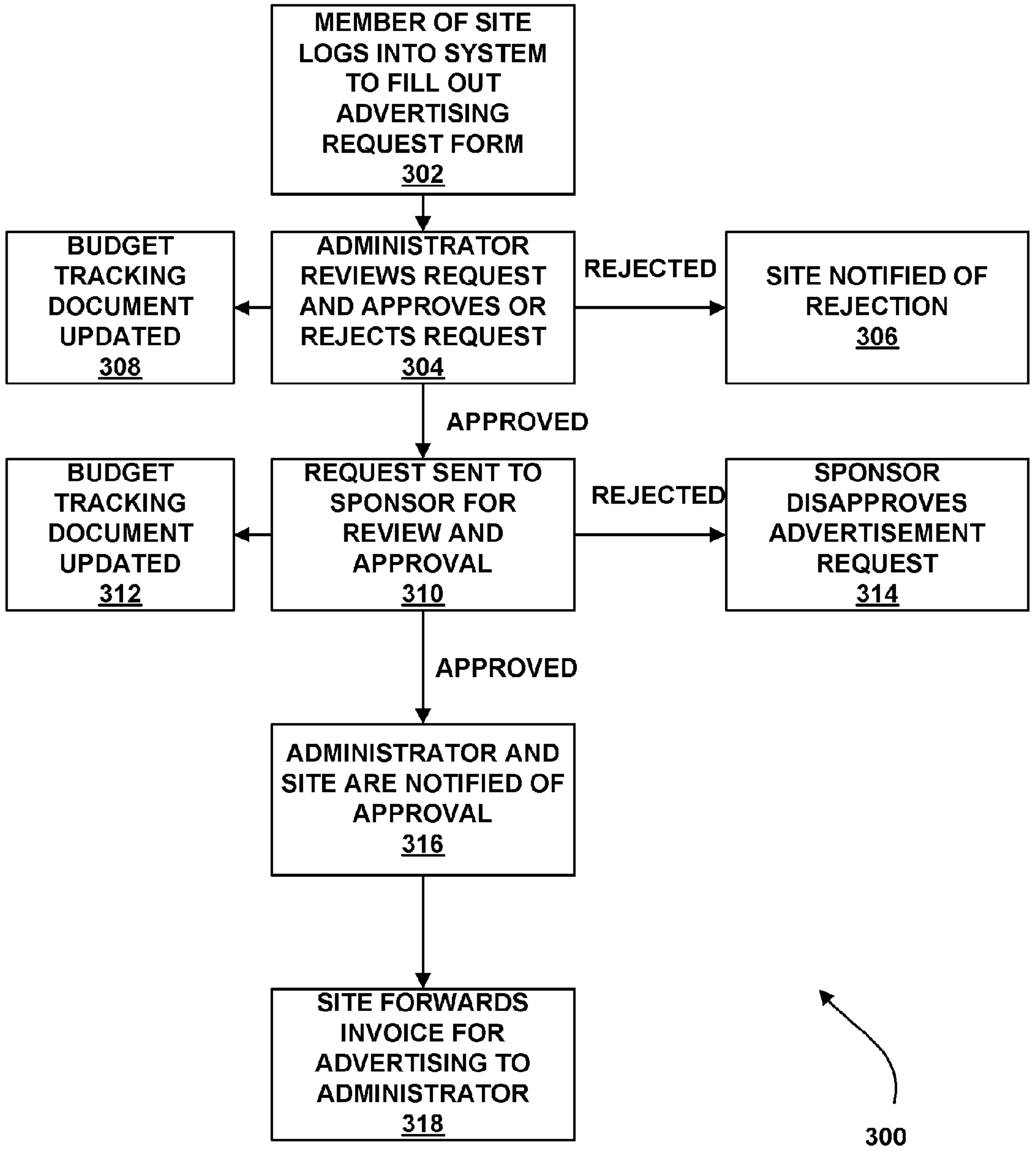
FIG. 4 is a flowchart exemplifying financial management as provided by the media manager of FIG. 2.

An example of financial management, as provided for by the media manager 140, is shown by the flowchart 300 of FIG. 4. It should be noted that FIG. 4 is an example and is not intended to limit scope of the present invention. As is shown by FIG. 4, a member of an investigatory site logs into the patient recruitment system 10 to fill out an electronic advertising request form (block 302). The electronic advertising request form may allow for selection of a type of advertising medium that will be used by the investigatory site such as, but not limited to, print, radio, television, direct mailing, or other advertisement. Other information may also be provided on the electronic advertising request form, or provided separate from the electronic advertising request form. As an example, the investigatory site may provide information such as, but not limited to, how long the advertisement will run, how many times the advertisement will run, how many patients are anticipated as being recruited by the advertisement, and what is the cost of the advertisement.

As is shown by block 304, the administrator of the patient recruitment system 10 reviews the advertising request and approves or rejects the request. If the advertisement request is rejected, the investigatory site is notified of the rejection (block 306). The rejection notice may be provided by one of many different means such as, but not limited to, an electronic mail (email) submission to the investigatory site or a mailed letter. Alternatively, if the advertising request is approved by the administrator, a budget tracking document is automatically updated so as to monitor potential costs (block 308).

Administrator approved advertisement requests are sent to the sponsor for review and approval (block 310). After forwarding administrator approved advertisement requests to the sponsor the budget tracking document is again automatically updated (block 312) so as to calculate expenditures on an investigatory site-by-site basis and against an overall advertising campaign budget. The sponsor may also receive the budget tracking document summarizing committed, invoiced, and remaining dollars available for advertising.

As is shown by block 314, the sponsor may disapprove of the advertisement request. Alternatively, if the sponsor approves of the advertisement request, the administrator and the investigatory site are electronically notified of the approval (block 316). Of course, notice of the approval may be provided in a manner that does not involve electronic notification. Once the advertisement request is approved, the investigatory site forwards an invoice for the advertising to the administrator (block 318). Status of the advertising request may then be changed on the document from “committed” to “invoiced.”

As mentioned above, the media manager 140 is also used to handle ROI. Specifically, investigatory sites project how many patients they assume that a patient outreach will yield. Once the patient outreach begins, the investigatory sites enter inquiry data into the patent recruitment system 10 (FIG. 6, FIG. 7, and FIG. 8, which illustrate functionality of a patient manager) and ROI tracking begins. Timely reports are automatically updated with this data. Such time periods may be weekly, bi-weekly, monthly, or any other time period that is beneficial.

Figure 5:
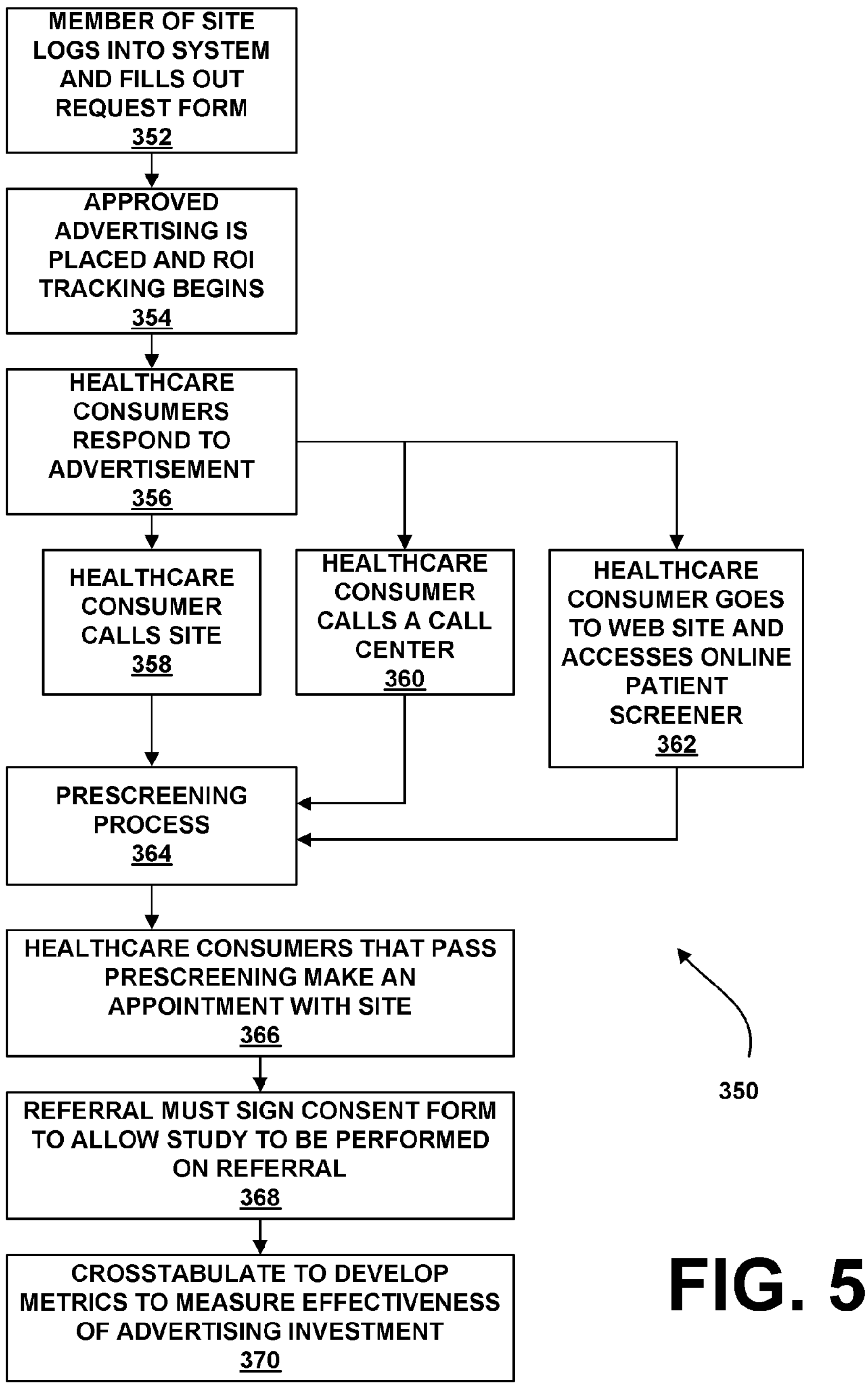
FIG. 5 is a flowchart illustrating a return-on-investment process as performed by the media manager of FIG. 2.

FIG. 5 is a flowchart 350 better illustrating the ROI tracking process. Sponsors can review performance of patient outreach on a site-by-site basis as well as by an entire study community. The patent recruitment system 100 tracks patient referrals by outreach vehicle (e.g., advertisements), and then cross-tabulates that data with actual cost of outreach vehicle placement. The patient recruitment system 100 also creates metric reports by media type and by site. The patient recruitment system 100 calculates per-patient cost for each outreach initiative and provides sponsors with financial data per patient recruitment tactic, as well as per patient.

It should be noted that FIG. 5 provides an example of the ROI tracking process and is not intended to be limiting. The ROI tracking process assists in linking the requested amount desired for advertising, to the actual amount spent on advertising, to an actual number of patients enrolled in a trail. As is shown by block 352, a member of an investigatory site logs into the patient recruitment system 100 and fills out an electronic advertising request form. During filling out of the electronic advertising request form, the member enters a projection of how many patients they believe will enter the study from the advertising. The approved advertising is then placed and ROI tracking begins 354.

Healthcare consumers then respond to the advertisements (block 356) and all responses are captured and classified as an inquiry. Healthcare consumers may respond to the advertisements by either calling the investigatory site (block 358), calling a call center responsible for reporting to the investigatory site (block 360), or responding to the advertisement by going to a Web site and accessing an online patient screener (block 362). Responses to advertising are classified as inquiries and are captured by the patient recruitment system 100.

Healthcare consumers that respond to the advertisement are subjected to a prescreening process to determine if the consumer qualifies for the treatment associated with the patient recruitment (block 364). It should be noted that the prescreening process is further described and illustrated with regard to FIG. 6, FIG. 7, and FIG. 8, which are focused on a patient manager. Healthcare consumers that pass the prescreener are classified by the media manager 140 as a referral. A first appointment with the site is made for the referrals (block 366), which is when further screening of the referral may be performed to ensure that the referral may be subjected to proposed treatment.

It is a requirement for the referral to sign a consent form to allow the study to be performed on the referral (block 368). It should be noted that referrals that sign an informed consent form are classified by the patient recruitment system 100 as patients. The patient recruitment system 100 may then track inquiries, referrals, and patients by advertising vehicle. In addition, the patient recruitment system 100 may cross-tabulate the tracked inquiries, referrals, and patients with actual cost to develop metrics to measure effectiveness of advertising investment (block 370). Timely reports may also be generated and reviewed by sponsors on the performance of each advertising type, as well as, reports that calculate cost of inquiry, referral, and patient.

The media manager 140 also links to the document manager 132 and regulatory manager 134, thereby assuring that only approved materials are allowed for use in advertising.

Returning to FIG. 2, the software 100 also defines search record accessibility 150. Specifically, in accordance with the present invention data fields are easily and dynamically accessible through a search engine. This search engine self-generates database queries depending on user-defined search criteria. Each set of search criteria can be saved and shared with other users of the patient recruitment system 10 depending on security levels associated with a patent recruitment system login.

Among the many different reports that may be made available by the present patient recruitment system 10, analysis reports and metric reports may be provided. Analysis reports are static data created in a moment in time on any data point in the storage device. A sponsor can track and save comparative data to a point in time (e.g., on May 1, how many patients were consented in Boston, Mass.). In addition, a sponsor can track and save comparative data over time.

Metric reports are dynamic data created on any data point in the storage device 15. Once reports are generated, the reports automatically incorporate new data each time the report is run (e.g., track how many patients are consented in Boston, Mass., which will automatically change as enrollment changes).

The software 100 also defines a patient manager 160. The patient manager 160 tracks patients from original patient inquiry through consent provided by a patient, assisting investigatory sites with managing the entire patient enrollment process, while at the same time providing sponsors with key intelligence into site activity prior to patient randomization in a study. The functionality provided by the patient manager is exemplified by the flowchart 400 of FIG. 6, the flowchart 450 of FIG. 7, and the flowchart 500 of FIG. 8.

Functionality of the patient manager 160 may be separated into a pre-screener portion and a patient status portion. The prescreener portion of the patient manager 160 is a customized electronic questionnaire. The purpose of the prescreener portion is to determine if a healthcare consumer is a potential patient for a clinical study. As an example, the electronic questionnaire may contain ten to twenty questions. Of course, more or fewer questions may be used. The prescreener portion is preferably programmed to skip to a close statement if a question is answered in a way that would disqualify the patient from the clinical study. This process may be performed through branch logic that is embedded in the prescreener portion. The branch logic dictates what page (question or close statement) is displayed to the potential patient, based upon the answer provided by the potential patient (i.e., healthcare consumer). If a healthcare consumer answers the pre-screener questionnaire in a way that would qualify the healthcare consumer for the study, then the patient manager 160 requests full contact information of the healthcare consumer. Once submitted, the contact information of this new patient, and his/her answers, are saved as a lead sheet in a patient table and associated with a specific investigatory site.

The purpose of the patient status portion is to associate a status with a potential patient at all times. Each healthcare consumer entered into the patient recruitment system 10 is tagged with a status. The status is an indicator of where in the patient enrollment phase the potential patient presently stands. Once a site opens a new patient referral for a potential patient, the status of the potential patient automatically changes to reflect that the referred potential patient has been received at the site. Reports may be generated dynamically as patient statuses are changed. Sponsors then can receive real-time information on the recruitment status of each investigatory site.

Figure 6:
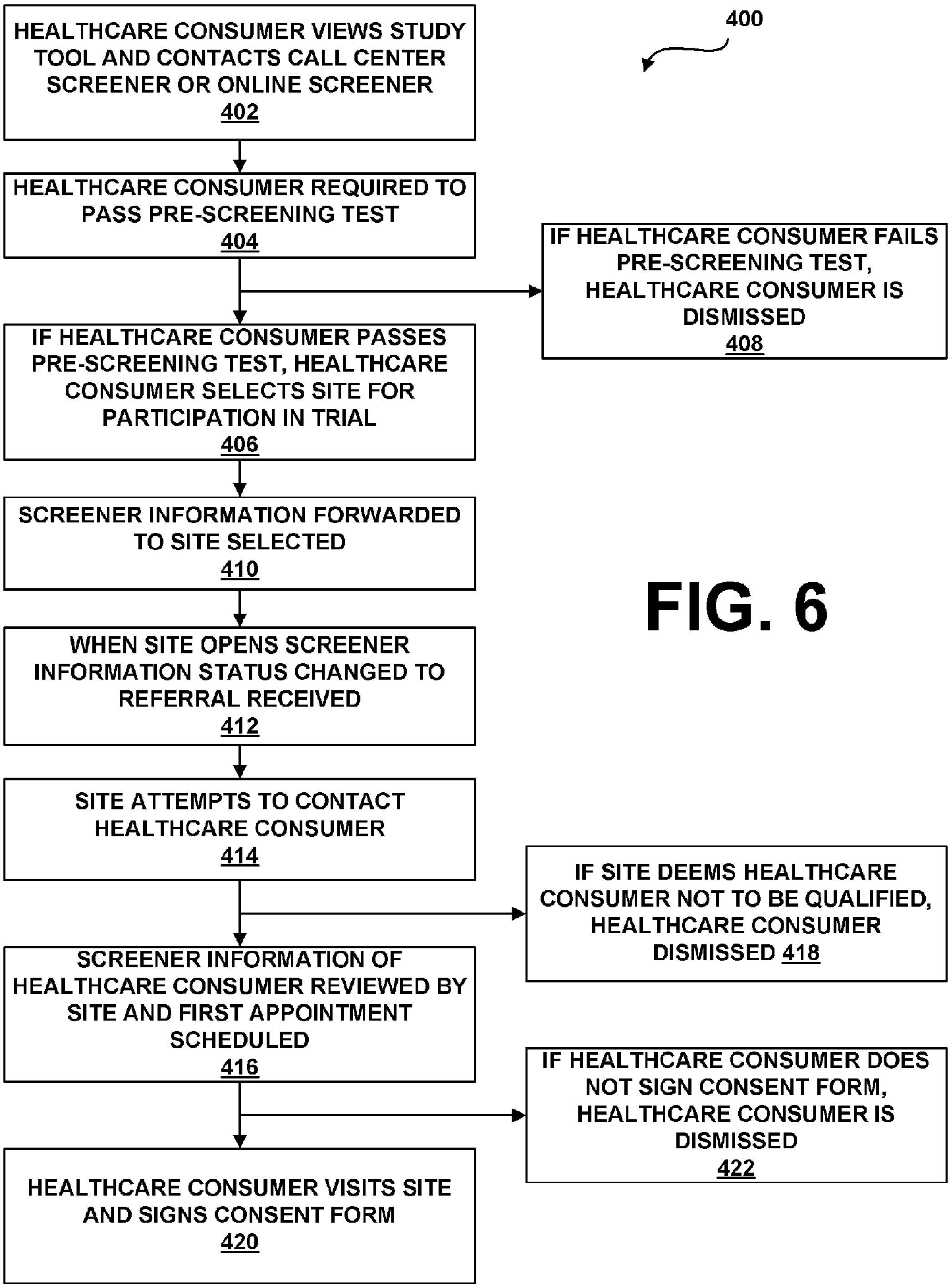
FIG. 6 is a flowchart illustrating functionality performed by the patient manager of FIG. 2 when a call-center is involved.
Figure 7:
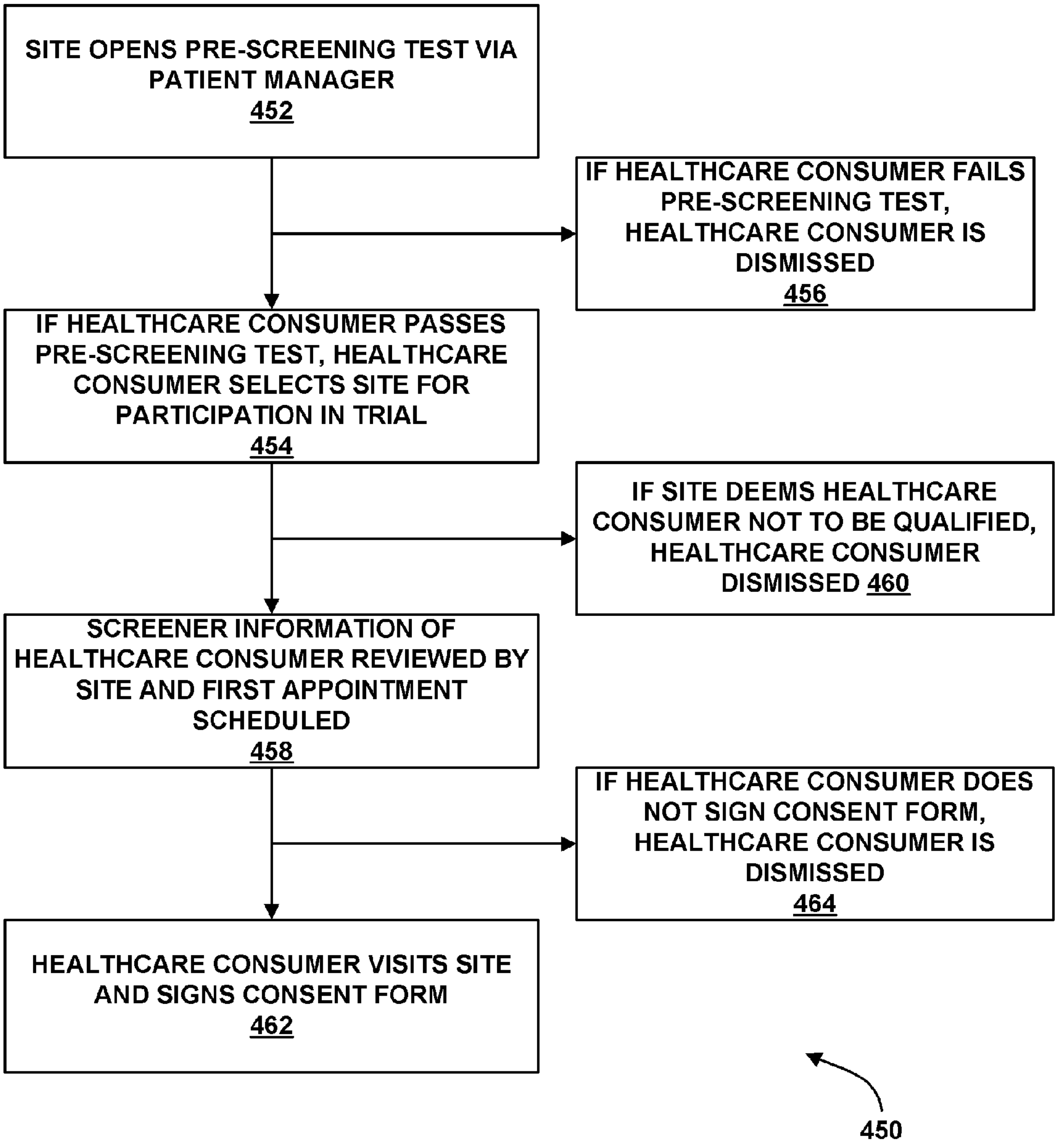
FIG. 7 is a flowchart illustrating functionality performed by the patient manager of FIG. 2 when a potential patient contacts an investigatory site directly.
Figure 8:
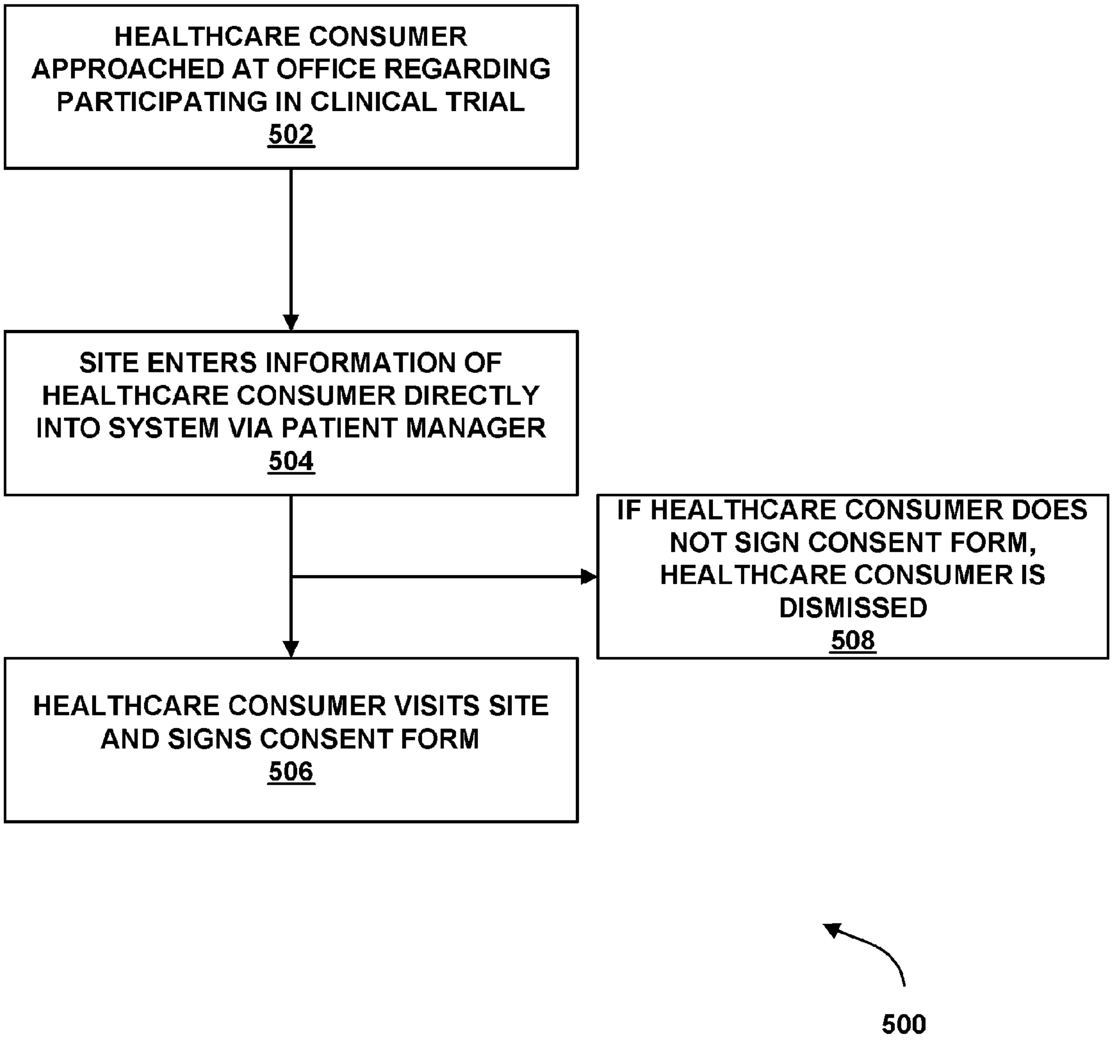
FIG. 8 is a flowchart illustrating functionality performed by the patient manager of FIG. 2 when a potential patient is approached regarding participating in a clinical study while at a medical facility.

As mentioned above, functionality provided by the patient manager is exemplified by the flowchart 400 of FIG. 6, the flowchart 450 of FIG. 7, and the flowchart 500 of FIG. 8. Specifically, the flowchart 400 of FIG. 6 illustrates functionality of the patient manager 160 when a call-center is involved; the flowchart 450 of FIG. 7 illustrates functionality of the patient manager 160 when a potential patient contacts an investigatory site directly; and the flowchart 500 of FIG. 8 illustrates functionality of the patient manager 160 when a potential patient is approached about participating in a study while the potential patient is at an office, such as the office of a doctor.

Referring to FIG. 6, a healthcare consumer views a study tool such as, but not limited to, an advertisement, and the healthcare consumer contacts a centralized call center screener or an online screener (block 402). The healthcare consumer is then required to pass a pre-screening test (block 404). If the healthcare consumer passes the pre-screening test, the healthcare consumer selects an investigatory site in their area for participating in the clinical trial (block 406). Alternatively, if the healthcare consumer fails the pre-screening test, the healthcare consumer is dismissed and not allowed to participate in the clinical trial (block 408).

When a healthcare consumer passes the pre-screening test, the screener information of the healthcare consumer is forwarded, via the patient recruitment system 10, to the investigatory site selected and status of the healthcare consumer is designated as a new referral (block 410). When the investigatory site opens the screener information of the healthcare consumer to review the information, status of the healthcare consumer is changed to referral received (block 412). The investigatory site may then attempt to contact the healthcare consumer, wherein results of the attempted contact may be stored in the storage device 15 by the patient manager 160 (block 414).

Screener information of the healthcare consumer is then reviewed by the investigatory site, after which a first appointment with the healthcare consumer is scheduled (block 416). If, however, the investigatory site deems the healthcare consumer not to be qualified, the healthcare consumer is dismissed (block 418). The healthcare consumer then visits the investigatory site, or a site designated by the investigatory site, and signs a consent form, thereby consenting to his/her participation in the clinical trial (block 420). If, however, the healthcare consumer does not sign the consent form, the healthcare consumer is dismissed (block 422).

Referring to FIG. 7, the flowchart 450 of which illustrates functionality of the patient manager 160 when a healthcare consumer contacts an investigatory site directly, the investigatory site opens the pre-screening test via use of the patient manager 160 (block 452). If the healthcare consumer passes the pre-screening test, the healthcare consumer selects an investigatory site in their area for participating in the clinical trial (block 454). Alternatively, if the healthcare consumer fails the pre-screening test, the healthcare consumer is dismissed and not allowed to participate in the clinical trial (block 456).

Screener information of the healthcare consumer is then reviewed by the investigatory site, after which a first appointment with the healthcare consumer is scheduled (block 458). If, however, the investigatory site deems the healthcare consumer not to be qualified, the healthcare consumer is dismissed (block 460). The healthcare consumer then visits the investigatory site, or a site designated by the investigatory site, and signs a consent form, thereby consenting to his/her participation in the clinical trial (block 462). If, however, the healthcare consumer does not sign the consent form, the healthcare consumer is dismissed (block 464).

Reference is now made to the flowchart 500 of FIG. 8. As mentioned above, FIG. 8 illustrates functionality of the patient manager 160 when a potential patient is approached about participating in a study while the potential patient is at an office, such as a medical office, the office of a doctor, or a clinic. As is shown by block 502, the healthcare consumer is approached at the office about participating in the clinical trial. The investigatory site then enters the information of the healthcare consumer directly into the patient recruitment system via the patient manager 160 (block 504).

The healthcare consumer then visits the investigatory site, or a site designated by the investigatory site, and signs a consent form, thereby consenting to his/her participation in the clinical trial (block 506). If, however, the healthcare consumer does not sign the consent form, the healthcare consumer is dismissed (block 508).

After receiving consent, in the case where the healthcare consumer calls a call center, calls an investigatory site directly, and in the case where the healthcare consumer is at an investigatory site and is approached, status of the healthcare consumer is tracked and the healthcare consumer is assigned to a clinical trial. It should be noted that the sponsor receives automated reports tracking all patients from point of new referral through endpoints of the clinical trial. In addition investigatory sites receive automated reports tracking their patients from point of new referral though endpoints of the clinical trial. Further monitors receive automated reports tracking patients of their site from point of new referral through endpoints of the clinical trial.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and, principles of the invention. All such modifications and variations are intended to be included herein within the scope of this disclosure and the present invention and protected by the following claims.

We claim:

1. A system for gathering, managing, and analyzing patient recruitment, comprising:

logic embodied on at least one non-transitory computer readable medium configured to receive patient marketing material from a source;

logic embodied on at least one non-transitory computer readable medium configured to determine whether the patient marketing material is approved for use by a system administrator;

logic embodied on at least one non-transitory computer readable medium configured to provide the patient marketing material to a sponsor of a clinical study requiring patient recruitment, where the patient marketing material is provided to the sponsor for approval by the sponsor;

logic embodied on at least one non-transitory computer readable medium configured to determine if regulatory approval of the patient marketing material is required;

logic embodied on at least one non-transitory computer readable medium configured to make the patient marketing material available to a patient investigatory site for use in recruiting a patient for the clinical study; and logic embodied on at least one non-transitory computer readable medium configured to prescreen a healthcare consumer that responds to the patient marketing material.

2. The system of claim 1, wherein providing of patient marketing material to a sponsor is performed by making the patient marketing material available to the sponsor on a Web site.

3. The system of claim 1, wherein the patient marketing material is a first version of the patient marketing material and wherein the system further comprises logic embodied on at least one non-transitory computer readable medium for forwarding the first version of the patient marketing material to the source for editing, if the system administrator does not approve the patient marketing material for use.

4. The system of claim 1, wherein the patient marketing material is a first version of the patient marketing material and wherein the system further comprises logic embodied on at least one non-transitory computer readable medium for forwarding the first version of the patient marketing material to the system administrator for editing, if the sponsor does not approve the patient marketing material for use.

5. The system of claim 1, further comprising logic embodied on at least one non-transitory computer readable medium configured to prevent the patient marketing material from being available to the patient investigatory site if regulatory approval of the patient marketing material is required and the patient marketing material does not meet regulatory approval.

6. The system of claim 1, wherein making the patient marketing material available to the patient investigatory site is performed by making the patient marketing material available to the patient investigatory site on a Web site.

7. The system of claim 1, further comprising logic embodied on at least one non-transitory computer readable medium configured to determine a return-on-investment associated with use of the patient marketing material by the patient investigatory site.

8. The system of claim 1, further comprising logic embodied on at least one non-transitory computer readable medium configured to develop metrics to measure effectiveness of an advertising investment associated with the investigatory site providing the patient marketing material.

9. The system of claim 1, wherein the logic embodied on at least one non-transitory computer readable medium configured to prescreen the healthcare consumer uses a Web site to prescreen the healthcare consumer.

10. The system of claim 1, further comprising logic embodied on at least one non-transitory computer readable medium configured to take investigatory site initiation data (SID), that is either inputted directly or received from a secondary source, and link the data to investigatory site randomization data and patient screening data.

11. The system of claim 1, further comprising logic embodied on at least one non-transitory computer readable medium configured to provide the sponsor with automated reports tracking patients from a point of new referral through endpoints of the clinical study.

12. The system of claim 1, further comprising logic embodied on at least one non-transitory computer readable medium configured to provide the investigatory site with automated reports tracking their patients from a point of new referral though endpoints of the clinical study.

* * * * *